(12) United States Patent
Haak et al.

(10) Patent No.: US 6,317,629 B1
(45) Date of Patent: *Nov. 13, 2001

(54) IONTOPHORETIC DRUG DELIVERY APPARATUS

(75) Inventors: Ronald P. Haak; J. Richard Gyory, both of San Jose; Robert M. Myers, Menlo Park; Felix A. Landrau, San Jose; Harold F. Sanders, La Jolla; Lothar W. Kleiner, Los Altos; Linda M. Hearney, Saratoga, all of CA (US)

(73) Assignee: Alza Corporation, Mountain View, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/351,381

(22) PCT Filed: Jun. 1, 1993

(86) PCT No.: PCT/US93/05162

§ 371 Date: Dec. 2, 1994

§ 102(e) Date: Dec. 2, 1994

(87) PCT Pub. No.: WO93/24178

PCT Pub. Date: Dec. 9, 1993

Related U.S. Application Data

(63) Continuation-in-part of application No. 07/892,258, filed on Jun. 2, 1992, now abandoned.

(51) Int. Cl.[7] ..................................................... A61N 1/30
(52) U.S. Cl. ............................ 604/20; 607/152; 607/153; 439/86
(58) Field of Search ................................ 439/909, 91, 67, 439/86; 174/117 A; 604/20; 607/152–153

(56) References Cited

U.S. PATENT DOCUMENTS 4,474,570 * 10/1984 Ariura et al. .
4,744,787 * 5/1988 Phipps et al. .

FOREIGN PATENT DOCUMENTS

2170365 * 1/1986 (GB).
90/09413 * 8/1990 (WO).

* cited by examiner

Primary Examiner—Mark Bockelman
(74) Attorney, Agent, or Firm—D. Byron Miller; Owen J. Bates

(57) ABSTRACT

An iontophoretic delivery device (10) is provided. Device (10) has an electronic circuit (32) having electronic components such as batteries (30) mounted thereon. Device (10) also includes a pair of electrode assemblies (18, 19). The electronic circuit (32) is electrically connected to the electrode assemblies (18, 19) using an electrically conductive adhesive (34). The adhesive can also be used to electrically connect two or more electronic components within circuit (32) or to connect an electronic component to the electronic circuit (32). In one practice of the invention, the electrically conductive adhesive (44) functions as an electrode and electrically connects the circuit (32) to an agent-containing reservoir (24, 25). In a further practice of the invention, the electrically conductive adhesive (93) functions as an agent reservoir and contains the agent to be iontophoretically delivered.

24 Claims, 3 Drawing Sheets

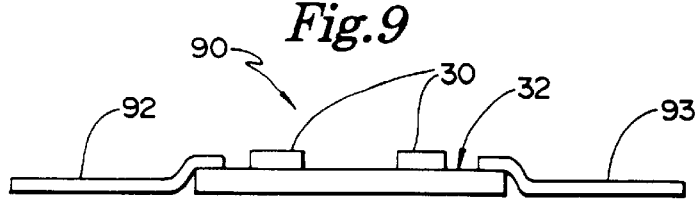
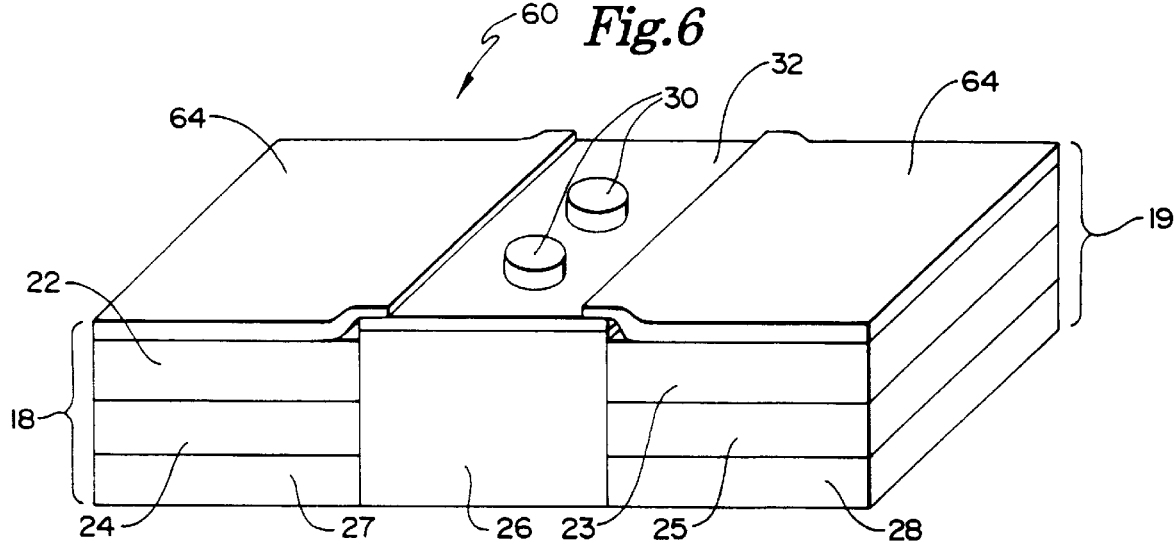
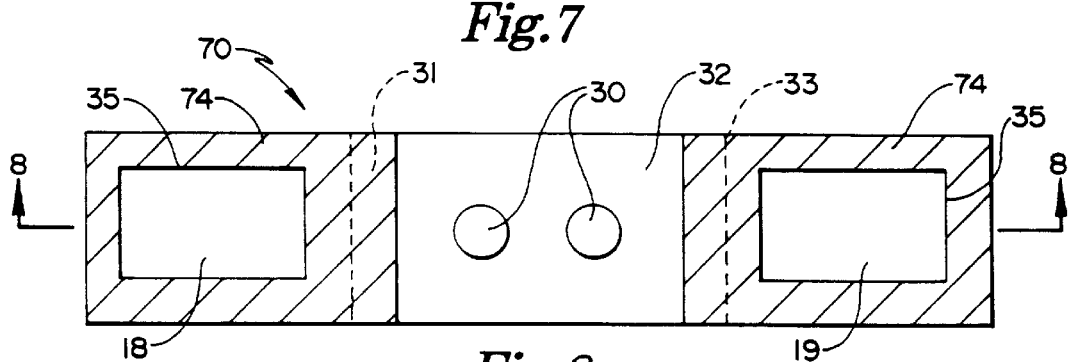
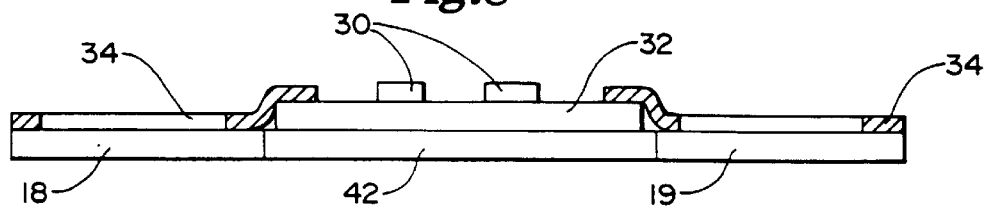

IONTOPHORETIC DRUG DELIVERY APPARATUS

This is a continuation-in-part of U.S. patent application Ser. No. 07/892,258 filed Jun. 2, 1992, now abandoned and a rule 371 National stage application of PCT/US 93/05162 filed Jun. 1, 1993.

TECHNICAL FIELD

The present invention generally concerns an apparatus for the electrically assisted delivery of a therapeutic agent. This invention also concerns a method for making such an apparatus.

More specifically, this invention concerns a flexible apparatus for iontophoretic drug delivery having at least two components which are electrically connected in a novel, inexpensive, yet reliable manner. Preferably, the apparatus has an electronic circuit which is electrically connected to another component or sub-assembly of the apparatus in this same novel, inexpensive, yet reliable manner.

BACKGROUND OF THE INVENTION

The present invention concerns apparatuses for transdermal delivery or transport of therapeutic agents, typically through iontophoresis. Herein the terms "iontophoresis" and "iontophoretic" are used to refer to methods and apparatus for transdermal delivery of therapeutic agents, whether charged or uncharged, by means of an applied electromotive force to an agent-containing reservoir. The particular therapeutic agent to be delivered may be completely charged (i.e., 100% ionized), completely uncharged, or partly charged and partly uncharged. The therapeutic agent or species may be delivered by electromigration, electroosmosis or a combination of the two. Electroosmosis has also been referred to as electrohydrokinesis, electro-convection, and electrically-induced osmosis. In general, electroosmosis of a therapeutic species into a tissue results from the migration of solvent, in which the species is contained, as a result of the application of electromotive force to the therapeutic species reservoir.

As used herein, the terms "iontophoresis" and "iontophoretic" refer to (1) the delivery of charged drugs or agents by electromigration, (2) the delivery of uncharged drugs or agents by the process of electroosmosis, (3) the delivery of charged drugs or agents by the combined processes of electromigration and electroosmosis, and/or (4) the delivery of a mixture of charged and uncharged drugs or agents by the combined processes of electromigration and electroosmosis.

Iontophoretic devices for delivering ionized drugs through the skin have been known since the early 1900's. Deutsch U.S. Pat. No. 410,009 (1934) describes an iontophoretic device which overcame one of the disadvantages of such early devices, namely that the patient needed to be immobilized near a source of electric current. The Deutsch device was powered by a galvanic cell formed from the electrodes and the material containing the drug to be transdermally delivered. The galvanic cell produced the current necessary for iontophoretically delivering the drug. This device allowed the patient to move around during iontophoretic drug delivery and thus imposed substantially less interference with the patient's daily activities.

In presently known iontophoresis devices, at least two electrodes are used. Both of these electrodes are disposed so as to be in intimate electrical contact with some portion of the skin of the body. One electrode, called the active or donor electrode, is the electrode from which the ionic substance, agent, medicament, drug precursor or drug is delivered into the body via the skin by iontophoresis. The other electrode, called the counter or return electrode, serves to close the electrical circuit through the body. In conjunction with the patient's skin contacted by the electrodes, the circuit is completed by connection of the electrodes to a source of electrical energy, e.g., a battery. For example, if the ionic substance to be driven into the body is positively charged, then the positive electrode (the anode) will be the active electrode and the negative electrode (the cathode) will serve to complete the circuit. If the ionic substance to be delivered is negatively charged, then the cathodic electrode will be the active electrode and the anodic electrode will be the counter electrode.

Furthermore, existing iontophoresis devices generally require a reservoir or source of the beneficial agent or drug, preferably an ionized or ionizable species (or a precursor of such species) which is to be iontophoretically delivered or introduced into the body. Examples of such reservoirs or sources include a pouch as described in the previously mentioned Jacobsen U.S. Pat. No. 4,250,878, a pre-formed gel body as disclosed in Webster U.S. Pat. No. 4,382,529 and a generally conical or domed molding of U.S. Pat. No. 4,722,726 to Sanderson et al. Such drug reservoirs are connected to the anode or the cathode of an iontophoresis device to provide a fixed or renewable source of one or more desired species or agents.

Perhaps the most common use of iontophoresis today is in diagnosing cystic fibrosis by delivering pilocarpine transdermally. Iontophoretically delivered pilocarpine stimulates sweat production, the sweat is collected, and is analyzed for its chloride ion content. Chloride ion concentration in excess of certain limits suggests the possible presence of the disease.

A variety of methods for attaching an iontophoretic delivery device to the skin of a patient have been disclosed, including straps, adhesive overlays, and in-line ion-conducting adhesives. For example, Sibalis U.S. Pat. Nos. 4,557,723; 4,640.689; 4,622,031; 4,708,716; 4,713,050; and 4,878,892 describes transdermal iontophoretic drug applicators having a return electrode which is secured to the skin with a layer of an electrically conductive adhesive material (i.e., the layer designated 36 in FIG. 2 of U.S. Pat. No. 4,557,723). None of the above Sibalis patents disclose a specific composition for the skin-contacting, electrically conductive adhesive material.

PCT published application WO 90/09413 discloses ion-conducting skin contacting adhesives for securing iontophoretic drug delivery devices to the skin. The contact adhesives (eg., silicone adhesives) disclosed therein have a predominantly hydrophobic character which is modified by the addition of a hydrophilic, usually polymeric, material to the hydrophobic adhesive. The hydrophilic additive provides a plurality of water retaining pathways through the otherwise hydrophobic adhesive matrix. Drug ions or molecules are transported through the adhesive by way of these water retaining pathways by electromigration and/or electroosmosis. Thus, these adhesives can be used as "in-line" adhesive layers positioned between a drug-containing (donor) reservoir, or a salt-containing (counter) reservoir, and the skin.

In the devices of these patents, the electrical coupling of the various electronic components (e.g., resistors, current regulators, pulse generators, batteries, etc) has been accomplished using conventional electrical coupling means such as soldered electrical connections. Unfortunately, soldered electrical connections have a very poor tolerance for flexing.

This is a serious disadvantage in devices such as iontophoretic drug delivery devices adapted to be worn on the skin for extended periods of time, e.g., as long as a week or more. When flexible (i.e., nonrigid) iontophoretic drug delivery devices having conventional soldered electrical connections are worn for such extended periods of time, there is a tendency for the electrical connections to break due to the flexing encountered during the patient's body movements. Breakage of an electrical connection can render the device completely inoperative.

Another approach described by Sibalis in U.S. Pat. No. 4,856,188 uses a flexible plastic sheet coated on one side with an electrically conductive coating to connect a battery of an iontophoresis apparatus to the electrodes. The opposite side of the sheet has an adhesive coating. The sheet is folded to permit the conductive coating to contact the battery terminal and the electrode. This approach tends to produce stress points at the folds which can cause the conductive coating to crack which can render the device completely inoperative.

Thus, there has been a need in the art for a means for electrically connecting or coupling electrical components in a flexible iontophoretic delivery device, which connections are not susceptible to breaking upon flexing of the device and which provide good electrical continuity at low cost.

More recently, there has been an effort to develop miniaturized iontophoretic drug delivery devices which are adapted to be worn on the skin unobtrusively under a patient's clothing. The electrical components in such miniaturized iontophoretic drug delivery devices are also preferably miniaturized and may be in the form of either microchips or small printed circuits. While printed circuits are desirable from a cost standpoint, there have been difficulties encountered in electrically connecting the printed circuit to the electrode assemblies containing the agent to be delivered. Specifically, printed electronic circuits are formed by printing or otherwise depositing electrically conductive pathways on a flexible substrate, usually in the form of a polymer sheet. Electronic components, e.g., batteries, resistors, pulse generators, capacitors etc, are then electrically connected, e.g., by soldering, to the printed or deposited electrically conductive pathways to form a complete circuit. Thus, in a typical case, both the printed electrically conductive pathways, as well as all of the electronic components electrically connected thereto, are located on one side of the flexible substrate. Because of the non-uniform height and cross-section presented by the various electrical components within the completed circuit, there have been difficulties encountered in laminating drug and/or electrolyte reservoirs to the side of the flexible circuit having the printed electrically conducted pathways and the electrical components mounted thereon.

One solution to this problem is to laminate the drug and electrolyte reservoirs to the opposite side of the flexible substrate. Unfortunately, this presents a problem in electrically connecting the drug and electrolyte reservoirs to the circuit. Thus, there has been a need in the art for a means for electrically connecting or coupling electrode assemblies, including drug and electrolyte reservoirs, of an iontophoretic delivery device to an electronic circuit having electrically conductive pathways and individual electronic components provided on one surface thereof, which connections are not susceptible to breaking upon flexing of the device and which provides good electrical continuity at low cost.

DESCRIPTION OF THE INVENTION

Briefly, in one aspect, the present invention comprises an iontophoretic drug delivery apparatus or electrotransport system having a flexible, electrically conductive adhesive means matrix or an electrically conducted adhesive (ECA) for coupling components of the system. The electrically conductive adhesive means can be used to couple, electrically, any two or more electrical components of the system, but preferably is used to couple an electrical circuit (e.g., a printed circuit) to an electrode assembly.

In a preferred practice, the ECA means is used to couple an electrical circuit output to an electrode, e.g., an anode or a cathode. As discussed hereinafter, the electrode may be coupled to further structure, e.g., a drug or electrolyte reservoir.

In a particularly preferred practice, the ECA means or matrix comprises a composite which is formed by laminating at least one layer of an adhesive material to at least one electrically conductive web, mat or mesh. The lamination takes place under conditions which cause the adhesive material to flow into the web, mat or mesh, resulting in a composite ECA of relatively uniform cross-section.

In yet a further practice of this invention, the ECA may itself comprise an electrode which is used to electrically connect an electrical circuit output to either (1) a drug reservoir (in the case of a donor electrode assembly) or (2) an electrolyte salt reservoir (in the case of a counter electrode assembly). In this practice of the invention it is preferred that the ECA electrode contain an electrochemically reactive species which generates or consumes ions during operation of the ECA-electrode. In the case of an ECA anode, the electrochemically reactive species should be capable of undergoing electrochemical oxidation during operation of the ECA anode. In the case of an ECA-cathode, the electrochemically reactive species should be capable of undergoing electrochemical reduction during operation of the ECA cathode. In addition, the ECA-electrode should be ion-conducting as well as electrically conducting (i.e., electron-conducting). In order to render the ECA ion-conducting, a liquid solvent-retaining, usually hydrophilic material, is added to the ECA.

BRIEF DESCRIPTION OF THE DRAWINGS

A better understanding of the present invention as well as other objects and advantages thereof will become apparent upon consideration of the following detailed description especially when taken with the accompanying drawings, wherein like numerals designate like parts throughout, and wherein:

FIG. 6 is a perspective view of an alternative iontophoretic delivery device according to this invention.

FIG. 7 is a top view of an apparatus of the invention, illustrating a preferred ECA shape;

FIG. 8 is a side sectional view of the device of FIG. 7 taken along line 8—8 of FIG. 7; and FIG. 9 is a side sectional view of another apparatus according to the present invention.

MODES FOR CARRYING OUT THE INVENTION

Figure 1:
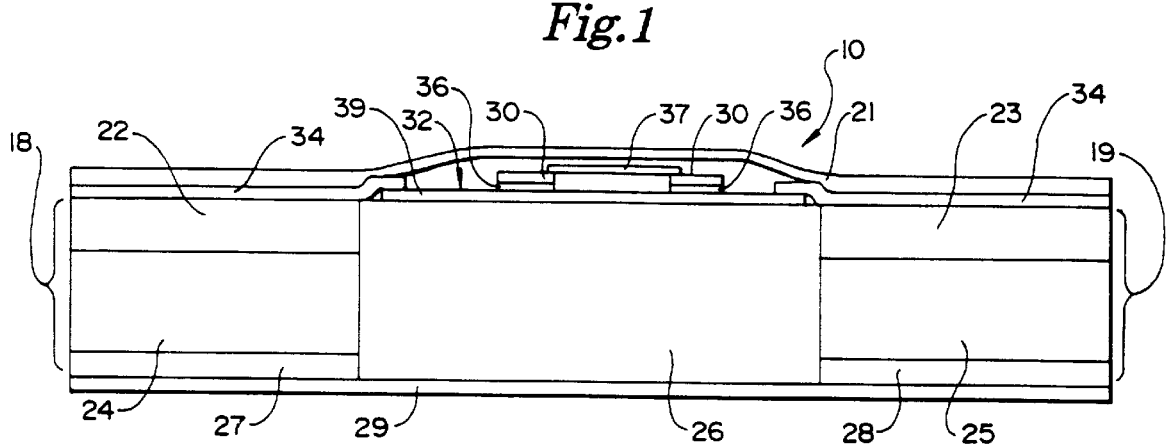
FIG. 1 is a side sectional view of an iontophoretic delivery device.

FIG. 1 is a schematic depiction of an iontophoretic delivery device 10. Device 10 can have essentially any convenient size or shape, whether square, oval, circular, or tailored for a specific location of the body. Device 10 is flexible and can easily conform to a body (e.g., skin) surface and flex with normal body movement. Device 10 has an electronic circuit 32 having batteries 30 mounted thereon. Generally, circuit 32 is relatively thin and preferably comprised of electronically conductive pathways printed, painted or otherwise deposited on a thin, flexible substrate 39 such as, for example, a film or polymeric web, e.g., circuit 32 is a printed flexible circuit. In addition, to the power source 30, circuit 32 may also include one or more electronic components which control the level, waveform shape, polarity, timing, etc. of the electric current applied by device 10. For example, circuit 32 may contain one or more of the following electronic components: control circuitry such as a current controller (e.g., a resistor or a transistor-based current control circuit), an on/off switch, and/or a microprocessor adapted to control the current output of the power source over time. Circuit 32 has two circuit outputs 31 and 33, each of which is overlain by a layer 34 of an electrically conductive adhesive (ECA). Circuit 32 and ECA layers 34 are preferably covered with a water-impermeable backing layer 21.

The term "flexible" when used herein to describe a device or a component of a device, means being capable of conforming to the contours if the area of the body to which the device is attached or to which it most closely approaches, i.e., to be conformable. "Flexible", as used herein, also means being capable of repeated bending, twisting, or deforming so as to continue to conform to the body throughout the normal range of patient movement and activity. For an entire device to be flexible, generally speaking, each of its individual components also must be flexible.

Device 10 includes two electrode assemblies indicated by brackets 18 and 19. Electrodes assemblies 18 and 19 are separated from one another by an electrical insulator 26, and form therewith a single self-contained unit. For purposes of illustration, the electrode assembly 18 is sometimes referred to as the "donor" electrode assembly while electrode assembly 19 is sometimes referred to as the "counter" electrode assembly. These designations of the electrodes assemblies are not critical and may be reversed in any particular device or in operation of the device shown.

In device 10, a donor electrode 22 is positioned adjacent a drug reservoir 24 while a counter electrode 23 is positioned adjacent a return reservoir 25 which contains an electrolyte. Electrodes 22 and 23 may comprise metal foils, or a polymer matrix loaded with metal powder, powdered graphite, carbon fibers, or any other suitable electrically conductive material. Reservoirs 24 and 25 can be polymeric matrices or gel matrices adapted to hold a liquid solvent. Aqueous-based or polar solvents, especially water, are generally preferred when delivering agents across biological membranes such as skin. When using an aqueous-based solvent, the matrix of reservoirs 24 and 25 is preferably comprised of a water retaining material and is most preferably comprised of a hydrophilic polymer such as a hydrogel. Natural or synthetic polymer matrices may be employed.

Insulator 26 is composed of a non-electrical conducting and non-ion-conducting material which prevents current (i.e., current in the form of either electrons or ions) from passing directly between electrode assemblies 18 and 19 thereby short circuiting the body to which the device is attached. Insulator 26 can be an air gap, a non-ion-conducting polymer or adhesive, or other suitable barrier to ion and electron flow.

The device 10 can be adhered to the skin by means of optional ion-conducting adhesive layers 27 and 28. The device 10 also preferably includes a strippable release liner 29 which is removed just prior to application of the device to the skin. Alternatively, device 10 can be adhered to the skin by means of an adhesive overlay of the type which are conventionally used in transdermal drug delivery devices. Generally speaking, an adhesive overlay contacts the skin around the perimeter of the device to maintain contact between reservoirs 24 and 25 and the patient's skin.

In a typical device 10, the drug reservoir 24 contains a neutral, ionized, or ionizable supply of the drug or agent to be delivered and the counter reservoir 25 contains a suitable electrolyte such as, for example, sodium chloride, potassium chloride, or mixtures thereof. Alternatively, device 10 can contain an ionizable, or neutral supply of drug in both reservoirs 24 and 25 and in that manner both electrode assemblies 18 and 19 would function as donor electrode assemblies. For example, positive drug ions could be delivered through the skin from the anode electrode assembly, while negative drug ions could be introduced from the cathode electrode assembly. Generally, the combined skin-contacting area of electrode assemblies 18 and 19 can range from about 1 $cm^2$ to about 200 $cm^2$, but typically will range from about 5 $cm^2$ to about 50 $cm^2$.

The drug reservoir 24 and return reservoir 25 of the iontophoretic delivery device 20 must be placed in agent or drug transmitting relation with the patient so as to iontophoretically deliver agent or drug. Usually this means the device is placed in intimate contact with the patient's skin. Various sites on the human body may be selected depending upon the physician's or the patient's preference, the drug or agent delivery regimen or other factors such as cosmetic.

Figure 2:
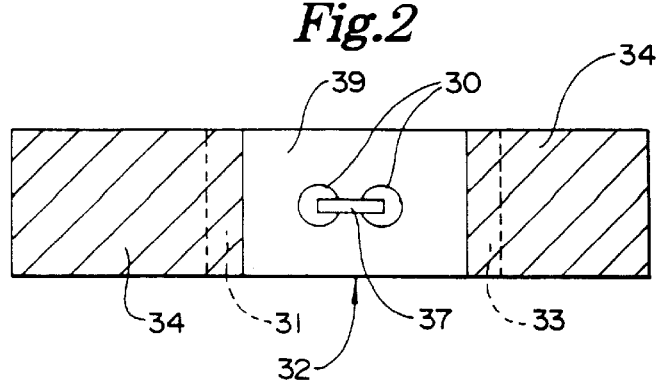
FIG. 2 is a top view of the device of FIG. 1.

FIG. 2 depicts a top view of the rectangularly-shaped, flexible device of FIG. 1 with the backing layer 21 removed for purposes of illustration. As shown, batteries 30 are electrically connected to the circuit 32. Circuit 32 has circuit output portions 31 and 33 which are each overlain by ECA 34.

Figure 5:
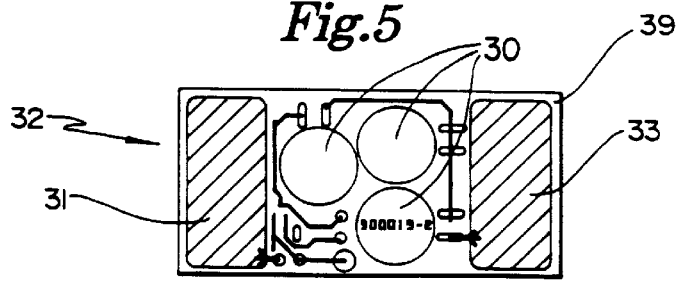
FIG. 5 is a top view of an electrical circuit useable in the present invention.

FIG. 5 illustrates one example of a flexible circuit 32 which can be utilized in the present invention. The circuit of FIG. 5 includes electrically conductive pathways which are printed or otherwise deposited on a thin flexible (e.g., polymeric) sheet 39. One or more electrical components including three button cell batteries 30 are mounted and connected to the conductive pathways of circuit 32. Circuit 32 also includes circuit outputs 31 and 33 on which the ECA can be applied in order to electrically connect the outputs 31 and 33 to the adjacent (usually underlying) electrode assemblies 18 and 19, respectively.

Generally speaking, the ECA 34 should be electrically conductive. The terms "electrically conductive" and "conductive" as used herein means having a bulk resistivity of less than about $1.5 \times 10^5$ ohm-cm, preferably less than about $10^3$ ohm-cm, and most preferably less than about 500 ohm-cm. The adhesive should be electrically conductive in all directions, i.e., in a direction parallel to the major surfaces of ECA 34 as well as in a direction perpendicular, thereto. In order to impart conductivity to an adhesive, an electrically conductive filler must generally be added to the adhesive. Examples of suitable electrically conductive fillers include carbon particles and fibers, metal flakes and powders such as silver, zinc or gold flakes and powders, conductive compounds such as silver chloride or silver oxide, or conductively coated polymer particles, e.g., silver coated polyvinylpyrrolidone particles. Conductive fibers in the form of a woven mat or web, a non-woven mat or web, or a conductive fabric may also be employed.

When using a conductive filler in particulate form, such as carbon powder, it is generally desirable to use the least amount of carbon powder as possible, such as 5 vol % or less, in order to retain maximum tack in the formulation. Therefore, the more conductive grades of carbon powder are preferred. The more conductive grades of carbon powder have an Iodine absorption number greater than 750 mg/g and preferably greater than 1000 mg/g. One particularly preferred carbon powder is Ketjenblack EC-600 JD produced by AKZO Chemicals, Inc., Chicago, Ill.

ECA 34 should also be adhesive, i.e., ECA 34 should be capable of adhering to both circuit 32 and the underlying electrode assembly. Generally speaking, the term "adhesive", when referring to a material, means that the material to which the term is applied has greater internal cohesion than external adhesion. Generally speaking, this means that substantially none of the adhesive material remains on a surface from which the adhesive is peeled. Pressure sensitive adhesives are a recognized class of materials which are "adhesive" as the term is used herein. "Adhesive" also means capable of causing one material, component, or layer to adhere to another.

The matrix of ECA 34 is preferably comprised of a polymer. The polymer itself can have adequate adhesive properties or it may be rendered suitably adhesive by the addition of tackifying resins. Suitable hydrophobic polymers include, without limitation, acrylic or methacrylic resins such as polymers of esters of acrylic or methacrylic acid with alcohols such as n-butanol, isopentanol, 2-methyl butanol, 1-methyl butanol, 1-methyl pentanol, 2-methyl pentanol, 3-methyl pentanol, 2-ethyl butanol, isooctanol, n-decanol, or n-dodecanol, alone or copolymerized with ethylenically unsaturated monomers such as acrylic acid, methacrylic acid, acrylamide, methacrylamide, N-alkoxymethyl acrylamides, N-alkoxymethyl methacrylamides, N-tert. butylacrylamide, itaconic acid, vinylacetate, N-branched alkyl maleic acids wherein the alkyl group had 10–24 carbon atoms, glycol diacrylates, or mixtures of these. Typical examples of commercially available acrylate adhesives suitable for use in this invention are the polyvinylacetate compounds sold by Monsanto Polymer Products Co. under the name of GELVA, such as GELVA 737 and GELVA 788, acrylate adhesives sold by the 3M Company such as 3M #9871 and 3M #9872, and sold by The Kendall Company under the name Kendall A200C-0. Also suitable are silicone adhesives which are prepared by the reaction of a linear polydimethylsiloxane fluid with a solvent-soluble, low molecular weight silicate resin. A typical example of a silicone adhesive suitable for use in this invention is a medical grade of silicone pressure-sensitive adhesive commercially available under the trademark DOW CORNING®355 Medical Grade Adhesive from Dow Corning Corporation. Plasticizers may also be added. A typical example is the addition of silicone medical fluid to the silicone adhesive.

Suitable polymers which can be rendered adhesive by the addition of tackifying resins include, without limitation, poly(styrene-butadiene) and poly(styrene-isoprene-styrene) block copolymers, ethylene vinyl acetate polymers such as those which are described in U.S. Pat. No. 4,144,317, plasticized or unplasticized polyvinylchloride, and natural or synthetic rubber, $C_2$–$C_4$ olefins such as polyethylene, polyisoprene, polyisobutylene and polybutadiene. Examples of suitable tackifying resins include, without limitation, fully hydrogenated aromatic hydrocarbon resins, hydrogenated esters and low molecular weight grades of polyisobutylene. Particularly suitable are tackifiers sold under the trademarks Staybelite Ester® #5 and #10, Regal-Rez® and Piccotac®, all of Hercules, Inc. (Wilmington, Del.).

Figure 4:
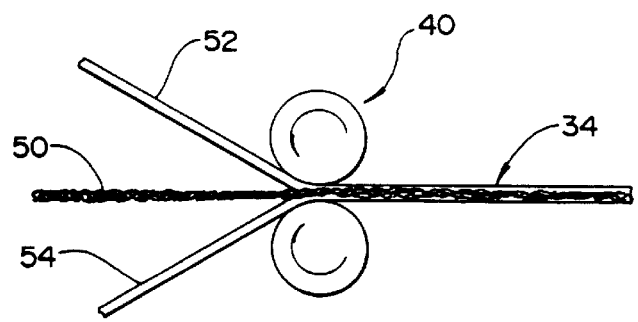
FIG. 4 is a side view of an apparatus for making a preferred composite electronically conductive adhesive material.

Although the ECA of the present invention is not limited to any particular structure or composition, one particularly preferred ECA is formed by laminating one or more layers 52, 54 of an adhesive material to one or more electrically conductive webs, mats or meshes 50 to form a composite ECA 34 as shown in FIG. 4. One particularly useful composite ECA 34 is formed by laminating between opposing laminating rollers 40 a single conductive mat or mesh 50 between two adhesive layers 52, 54. Lamination is conducted at a suitable temperature and pressure to ensure that layers 52 and 54 "flow" into the intersticial spaces between the fibers/strands of mesh 50 and intimately contact and adhere to the fibers/strands of mesh 50 so that the entire composite ECA 34 is flexible, adhesive, conductive and has a substantially uniform cross-section. A composite ECA (not shown) formed by laminating a single adhesive layer 52 to a single conductive mesh 50 is also suitable. An alternative composite ECA 34 (not shown) can be formed by laminating two conductive meshes 50 with a single layer 52 of adhesive sandwiched therebetween.

Mesh 50 is electrically conductive and preferably has a surface resistance of less than 10 ohms per square. The strands of the fabric may themselves be composed of an electrically conductive material (e.g., carbon fibers) or the fibers may be non-conductive (e.g., nylon fibers) which are coated with electrically conductive material such as graphite, carbon, silver, silver oxide, aluminum powder, or gold.

A particularly preferred composite ECA is formed by laminating at least one layer of an intermingled, non-woven, carbon fiber matting and at least one other layer of an adhesive polyisobutylene matrix. The non-woven carbon fiber matting can have a weight of about 3 to 70 $g/m^2$. The carbon fiber matting comprises about 1 to 10 volume percent, and preferably about 2 to 5 volume percent, of the total volume of the ECA. This ECA is made by laminating the polyisobutylene (PIB) into the carbon fiber mat so that the PIB flows therein and becomes intimately admixed therewith. Within the above limits, various equivalent formulations will become apparent to one of ordinary skill in this art. The preferred composite ECA may be produced by laminating the conductive mesh to one layer, or between two layers, of adhesive matrix. For example, sheet PIB, in rolled form, and kept usable by wrapping it with two release liners, is unrolled and laminated onto one or both major surfaces of a non-woven, conductive carbon mesh. In this manner, an ECA in sheet form, such as that shown in FIG. 4, is produced. The sheet can then be cut or otherwise processed into suitable lengths, shapes or configuration(s) for use in an electrotransport device.

Another ECA formulation comprises carbon fibers or carbon powder mixed or otherwise blended into either a silicone adhesive material or an acrylate adhesive material. For example, a formulation of 20 to 50 volume per cent (preferably about 25 to 45 volume per cent) carbon fiber, the remainder of the composition being the selected acrylate adhesive or silicone adhesive, provides an ECA which is highly flexible, has very low electrical resistivity and has reliable electrical continuity. The ECA can be cut or punched to form suitably sized strips from, e.g., a suitably rolled or calendared web or sheet of the ECA material.

Another ECA formulation comprises a mixture of high and low molecular weight polyisobutylene (PIB) intimately admixed with conductive carbon fibers or particles. Generally speaking, "high molecular weight" polyisobutylene, as the term is used herein, means polyisobutylene having a number average molecular weight of greater than about 800,000 and preferably greater than about 1,200,000. "Low molecular weight" polyisobutylene means polyisobutylene having a number average molecular weight in the range of about 10,000 to 50,000, preferably about 20,000 to 40,000. A preferred ratio of low molecular weight polyisobutylene to high molecular weight polyisobutylene is in the range of about 6:1 to 2:1, and most preferably about 5:1 to 3:1. As with the silicone/acrylate-based formulations described above, a formulation comprising about 20 to 50 volume per cent conductive carbon fibers or particles (preferably about 25 to 45 volume per cent carbon fibers or particles), the remainder comprising the polyisobutylene mixture, has been found particularly desirable.

Yet a further ECA formulation comprises a hydratable ECA which is useful in applications where either (i) the adhesive itself must contain a sufficient amount of a liquid solvent (i.e., a solvent for the agent being delivered, such as water) to render the ECA tonically conductive (i.e., able to support a flow of ions therethrough under the influence of an electric field); and/or (ii) the adhesive must be able to convey a liquid solvent (e.g., water) to an adjacent solvent-free reservoir or matrix (e.g., a dry drug reservoir or a dry electrolyte reservoir). Like other ECA's, the hydratable ECA may be in the form of a tape. A hydratable ECA formulation, generally speaking, contains an additive which is able to absorb the particular liquid solvent used to "hydrate" the ion-conducting portions of the electrotransport system. In most cases the liquid solvent is comprised of water and, hence, the additive is water absorbing. More preferabley, the additive comprises a hydrophilic polymer resin, most preferable a cross-linked hydrophilic polymer resin.

A preferred hydratable ECA formulation comprises the aforementioned high and low molecular weight polyisobutylene mixture intimately admixed with a conductivity enhancer such as conductive fibers, particles, or a conductive mat, and a hydratable macromolecular resin such as a hydrogel.

Batteries 30 may be electrically connected in series or in parallel to obtain the desired voltage and/or capacity necessary to obtain the electrophoretic action with the particular drug or agent. The exact orientation (i.e., polarity) of batteries 30 depends on whether the drug of choice is cationic or anionic. Any conventional small battery can be employed, arranged and connected in series or parallel to obtain the desired operating voltage and/or capacity. Of course, battery selection ultimately depends on such factors as the degree of flexibility or conformability desired, voltage and current density required for a specific application, and time of discharge.

The ECA described herein can also be used to electrically connect two or more electrical components (e.g., batteries 30) together or to electrically connect the battery output terminals to the electrical circuit. As shown in FIG. 1, ECA strip 37 is used to electrically connect one battery 30 to the other. In addition, ECA layers 36 are used to connect batteries 30 to electrical circuit 32.

ECA 34 is illustrated in FIGS. 1 and 2 as a rectangularly-shaped layer, however, any shape or configuration which adheres to the circuit outputs 31 and 33 and to the electrode assemblies 18 and 19, respectively, may be used. Lines, regions, frames, or other configurations of ECA can be employed, depending upon apparatus design. One particularly preferred shape for an ECA used to electrically connect circuit 32 to an underlying electrode assembly is illustrated in FIGS. 7–8. Device 70, like device 10, has two ECA's 74 which are used to electrically connect circuit outputs 31 and 33 to electrode assemblies 18 and 19. ECA's 74 are each in the shape of a window frame which contacts the underlying electrode assemblies 18 and 19, respectively, along the outer periphery thereof. Each ECA 74 has an opening 35 which is roughly centered over the top of each of the underlying electrode assemblies 18 and 19. When using a window frame shaped ECA 74, the underlying electroce assemblies 18 and 19 can be manufactured in a substantially non-hydrated condition. A hydrating liquid, typically water, can be added to the dry state electrode assemblies 18 and 19 just before use. The hydrating liquid can be applied, from either an external source or from an on-board liquid releasing means or container, directly through the openings 35 in the ECA 74. Optionally, a liquid wicking material (e.g., cotton gauze) can be placed within openings 35 in order to wick the hydrating liquid evenly across the top surfaces of dry state electrode assemblies 18 and 19.

An electrotransport system using this feature of the invention is made by first laminating a polymeric electrode, a drug or salt reservoir, and a skin contacting adhesive. This laminate is cut to the desired overall dimension(s). An ECAT then is die cut to the shape of a "window frame." This window frame is laminated to the electrode side of the laminate of electrode/drug or salt reservoir/skin adhesive, preferably about its perimeter or periphery. A piece of water wicking fabric cut to the same size as the inside dimensions of the window frame (i.e., the cut out portion) is then placed on top of the electrode. A flexible circuit may then be applied such that proper contact is made between the ECAT of two such electrode assemblies and the circuit. Finally, a backing is applied and edge sealed to the ECAT along the edge of the electrodes.

FIG. 6 shows an iontophoretic device 60 which, like device 70 illustrated in FIGS. 7 and 8, has an ECA which is permeable to a hydrating liquid to allow hydration of the underlying dry state electrode assemblies 18 and 19. Device 60 has two ECA layers 64 which are formulated to include an additive which renders layers 64 able to convey a hydrating liquid, preferably an aqueous hydrating liquid, therethrough. Any additive which can convey a hydrating liquid through the ECA layers 64 can be used. Since water is typically the liquid solvent used to conduct iontophoresis, a preferred class of additives are water absorbent additives, especially hydrophilic polymers or gels, for imparting water permeability to ECA layers 64. Most preferred are hydrophilic, water swellable but substantially water insoluble polymers, such as cross-linked polyvinylpyrrolidone. Typically, the ECA layers 64 contain from about 5 to 50 volume percent (preferably about 20 to 30 volume percent) of the hydrophilic polymer. The hydrophilic materials may be particulate or granular in nature, and preferably are non-ionic. Hydrophilic particles can be either water soluble or insoluble, but preferably are water insoluble. These particles function as a hydroattractant material, forming aqueous liquid conveying pathways through the generally hydrophobic adhesive. Suitable materials for the hydrophilic particles include, without limitation, polyacrylamide (PAA), Klucel®, cross-linked dextran such as Sephadex (Pharmacia Fine Chemicals, AB, Uppsala, Sweden), polyvinylalcohol (PVA), Waterlock A-180 (Grain Processing Corp., Muscatine, Iowa) which is a starch-graft-poly(sodium acrylate-co-acrylamide) polymer, cellulosic derivatives such as hydroxypropylmethylcellulose (HPMC), low-substituted hydroxypropylcellulose (LHPC) and cross-linked Na-carboxymethylcellulose such as Ac-Di-Sol (FMC Corp., Philadelphia, Pa.), hydrogels such as polyhydroxyethyl methacrylate (pHEMA) (National Patent Development Corp.), blends of polyoxyethylene or polyethylene glycols with polyacrylic acid such as Polyox® blended with Carbopol®, cross-linked polyvinyl pyrrolidone (PVP) (GAF Corporation), cholestyramine resins, natural gums and chitosan. Also suitable are phospholipids such as L-α-phosphatidylcholine (Sigma Chemical Company) which has both hydrophilic and hydrophobic properties. Blending of the hydrophobic, adhesive component and the hydrophilic, liquid conveying component can be done mechanically, either in solution or by milling. No polymerization or chemical alteration takes place. The resulting adhesive films are then prepared by extrusion and calendering, or by solvent casting, or by melt processing.

The addition of the liquid conveying additive allows transport of a liquid solvent (e.g., water) into and through the ECA layers 64. This enables device 60 to be manufactured in a substantially dry state, i.e., reservoirs 24 and 25 and adhesive layers 27 and 28 are manufactured and packaged in a substantially dehydrated condition. Manufacture and assembly of device components in a dehydrated state tends to improve the shelf life of a device containing a hydration-sensitive drug within reservoir 24 and/or 25. Of course, in order for device 60 to become operational, a liquid solvent such as water must be added to the ion-conducting portions of the device (e.g., reservoirs 24 and 25 and skin-contacting adhesive layers 27 and 28). The presence of a liquid solvent allows drug and/or other ions to migrate through the ion-conducting portions of device 60 under the influence of an electric field imposed by batteries 30. The dry adhesive layers 27 and 28 and the dry reservoirs 24 and 25 can be hydrated immediately before use by adding a liquid solvent (e.g., water) from either an external source or from an on-board liquid-releasing container (not shown) directly onto the top surface of ECA layers 64. The liquid is quickly conveyed through the ECA layers 64, as well as through the electrode layers 22 and 23 which are formulated to contain the same or similar water-conveying additive, and absorbed by the dry underlying layers 24, 25, 27 and 28 due to the presence of the hydrophilic water conveying additive.

Figure 3:
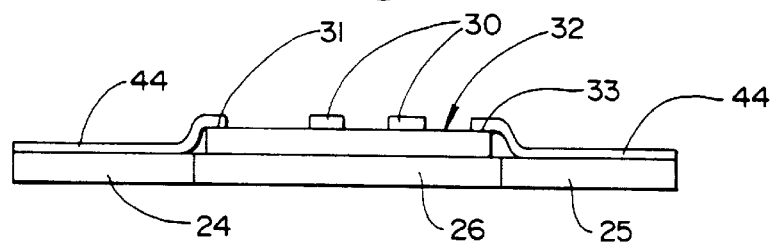
FIG. 3 is a side sectional view of an alternative device according to this invention.

In another practice of this invention, the ECA itself acts as an electrode, i.e., either as an anode or as a cathode. In this embodiment, the ECA preferably contains a material which is electrochemically reactive. In this practice, the ECA is used to electrically connect an electrical circuit to either a drug containing reservoir (in the case of a donor electrode assembly) or to a salt-containing reservoir (in the case of a counter electrode assembly). One example of an iontophoretic delivery device utilizing ECA electrodes 44 is illustrated in FIG. 3. As shown, ECA electrodes 44 electrically connect circuit outputs 31 and 33 to drug reservoir 24 and salt reservoir 25, respectively.

When the ECA electrode 44 is an anode, the electrochemically reactive material is capable of undergoing an electrochemical oxidation reaction. When the ECA electrode 44 is a cathode, the electrochemically reactive material is capable of undergoing an electrochemical reduction reaction. Examples of preferred oxidation/reduction reactions include the following:

$$Ag = Ag^+ + e^-$$

$$Zn = Zn^{+2} + 2e^-$$

$$Cu = Cu^{+2} + 2e^-$$

$$Ag + Cl^- = AgCl + e^-$$

$$Zn + 2Cl^- = ZnCl_2 + 2e^-$$

where the forward reaction is the oxidation reaction taking place at the anodic electrode and the reverse reaction is the reduction reaction taking place at the cathodic electrode. Other standard electrochemical reactions and their respective reduction potentials are well known in the art. See the CRC Handbook of Chemistry and Physics, pp D 151–58, 67th edition (1986–1987).

If the ECA electrode is to be used as an anode, the chemical species added to the ECA should be able to undergo oxidation during operation of the device. Suitable chemical species able to undergo oxidation include metals such as silver, zinc, copper, nickel, tin, lead, iron, chromium and other oxidizable species listed in the CRC Handbook of Chemistry and Physics, 57th edition, D-141 to D-146. Preferred chemical species able to undergo oxidation are metals, preferably in the form of powders. Most preferred are silver and zinc powders.

If the ECA electrode is to be used as a cathode, the chemical species added to the ECA should be able to undergo reduction during operation of the device. Suitable chemical species which are able to undergo reduction include silver chloride, silver bromide, silver hexacyanoferrate, and other reducible species listed in the CRC Handbook of Chemistry and Physics, 57th edition, D-141 to D-146. Of these, silver chloride powder is most preferred.

Preferably, the matrix of ECA electrodes 44 contains about 5 to 40 vol %, more preferably about 15 to 30 vol %, and most preferably about 20 to 25 vol % of the electrochemically reactive species.

In another practice of this invention, the ECA acts as a combined electrode (i.e., an anode or a cathode) and agent-containing reservoir (i.e., a drug reservoir in the case of a donor electrode or a salt reservoir in the case of a counter electrode). In this practice, the ECA contains the agent to be iontophoretically delivered. One example of a device configuration is illustrated in FIG. 9. In iontophoretic delivery device 90 illustrated in FIG. 9, the ECA layers 92 and 93 perform several functions. First, one of ECA layers 92 and 93 contains the drug to be delivered while the other contains an electrolyte salt. Thus, ECA layers 92 and 93 act as drug (donor) and salt (counter) reservoirs. Second, ECA layers 92 and 93 act as electrodes (i.e., anode and cathode) as well. Thus, one of the ECA layers 92 and 93 preferably contains an electrochemically oxidizable species (e.g., silver) while the other contains an electrochemically reducible species (e.g., silver chloride). Third, ECA layers 92 and 93 directly contact the skin and therefore act as a means for securing device 90 to the skin. Fourth, ECA layers 92 and 93 each form an electrical connection to circuit 32. Since the ECA layers perform both the functions of drug or salt reservoir and skin-contacting adhesive, each of ECA layers 92 and 93 must have a liquid solvent retaining additive of the type described in connection with ECA 64 (FIG. 6) in order to form liquid solvent (preferably aqueous solvent) pathways through the ECA matrix in order to allow ions (e.g., drug or electrolyte ions) to flow therethrough under the influence of an electrical field provided by the batteries 30.

The ECA layers 92 and 93 can be either in a dry or hydrated state when applied to the biological interface, depending upon the delivery profile desired or depending upon the stability of the other constituents, for example, the drug or the oxidizable or reducible species, when water is present. Utilizing the ECA layers 92 and 93 in a hydrated state may facilitate the onset of drug delivery as pathways for drug passage will be immediately available. Hydration of the ECA layers 92 and 93 can be accomplished in several ways. The ECA layers 92 and 93 can be hydrated before packaging it in or with the rest of the system. Alternately, the ECA layers 92 and 93 can be hydrated immediately prior to placement on the biological interface. Alternately, the aqueous source can be incorporated into the iontophoretic drug delivery system with a barrier separating the aqueous source from the ECA layers 92 or 93. At an appropriate time, e.g., immediately prior to use, the barrier is broken or removed so as to hydrate the ECA layers 92 or 93.

To function as a drug or electrolyte salt reservoir, the ECA must contain agent in an amount sufficient to maintain therapeutic delivery for an extended period of time. The ECA may also have other additives present such as are commonly known in the art. These include, plasticizers which may modify the tack and cohesive strength of the adhesive, fillers which may reduce the cost and improve handling, and antioxidants which improve the adhesive's resistance to oxidative degradation.

The terms "agent" or "drug" are used extensively herein. As used herein, the expressions "agent" and "drug" are used interchangeably and are intended to have their broadest interpretation as any therapeutically active substance which is delivered to a living organism to produce a desired, usually beneficial, effect. In general, this includes therapeutic agents in all of the major therapeutic areas including, but not limited to, anti-infectives such as antibiotics and antiviral agents, analgesics and analgesic combinations, anesthetics, anorexics, antiarthritics, antiasthmatic agents, anticonvulsants, anti-depressants, antidiabetic agents, antidiarrheals, antihistamines, anti-inflammatory agents, antimigraine preparations, antimotion sickness preparations, antinauseants, antineoplastics, antiparkinsonism drugs, antipruritics, antipsychotics, antipyretics, antispasmodics, including gastrointestinal and urinary, antispasmodics, anticholinergics, sympathomimetrics, xanthine derivatives, cardiovascular preparations including calcium channel blockers, beta-blockers, antiarrhythmics, antihypertensives, diuretics, vasodilators, including general, coronary, peripheral and cerebral, central nervous system stimulants, cough and cold preparations, decongestants, diagnostics, hormones, hypnotics, immunosuppressives, muscle relaxants, parasympatholytics, parasympathomimetrics, proteins, peptides, polypeptides and other macromolecules, psychostimulants, sedatives and tranquilizers.

The present invention can be used to iontophoretically deliver the following drugs: α-2b interferon, alfentanyl, amphotericin B, angiopeptin, baclofen, beclomethasone, betamethasone, bisphospionates, bromocriptine, buserelin, buspirone, calcitonin, ciclopirox olamine, copper, cromolyn sodium, desmopressin, diclofenac diflorasone, diltiazem, dobutamine, dopamine agonists, dopamine agonists, doxazosin, droperidol, enalaprilat fentanyl, encainide G-CSF, GM-CSF, M-CSF, GHRF, GHRH, gonadorelin, goserelin, granisetron, haloperidol, hydrocortisone, indomethacin insulin, insulinotropin, interleukin, isosorbide dinitrate, ketoprofen, ketoprofen, ketorolac, leuprolide, LHRH, lidocaine, lisinopril, LMW heparin, melatonin, methotrexate, metoclopramide, miconazole, midazolam, nafarelin, nicardipine, NMDA antagonists, octreotide, ondansetron oxybutynin, $PGE_1$, piroxicam, pramipexole, prazosin, prednisolone, prostaglandins, scopolamine, seglitide, sufentanil, terbutaline, testosterone, tetracaine, tropisetron, vapreotide, vasopressin, verapamil, warfarin, zacopride, zinc, zotasetron.

This invention is also believed to be useful in the iontophoretic delivery of peptides, polypeptides and other macromolecules typically having a molecular weight of at least about 300 daltons, and typically a molecular weight in the range of about 300 to 40,000 daltons. Specific examples of peptides and proteins in this size range include, without limitation, LHRH, LHRH analogs such as buserelin, gonadorelin, naphrelin and leuprolide, GHRH, insulin, heparin, calcitonin, endorphin, TRH, NT-36 (chemical name: N=[[(s)-4-oxo-2-azetidinyl]carbonyl]-L-histidyl-L-prolinamide), liprecin, pituitary hormones (e.g., HGH, HMG, HCG, desmopressin acetate, etc,), follicle luteoids, αANF, growth hormone releasing factor (GHRF), βMSH, TGF-β, somatostatin, atrial natriuretic peptide, bradykinin, somatotropin, platelet-derived growth factor, asparaginase, bleomycin sulfate, chymopapain, cholecystokinin, chorionic gonadotropin, corticotropin (ACTH), epidermal growth factor, erythropoietin, epoprostenol (platelet aggregation inhibitor), follicle stimulating hormone, glucagon, hirulogs, hyaluronidase, interferon, insulin-like growth factors, interleukin-2, menotropins (urofollitropin (FSH) and LH), oxytocin, streptokinase, tissue plasminogen activator, urokinasia, vasopressin, ACTH analogs, ANP, ANP clearance inhibitors, angiotensin II antagonists, antidiuretic hormone agonists, antidiurietic hormone antagonists, bradykinin antagonists, CD4, ceredase, CSF's, enkephalins, FAB fragments, IgE peptide suppressors, IGF-1, neuropeptide Y, neurotrophic factors, opiate peptides, parathyroid hormone and agonists, parathyroid hormone antagonists, prostaglandin antagonists, pentigetide, protein C, protein S, ramoplanin, renin inhibitors, thymosin alpha-1, thrombolytics, TNF, vaccines, vasopressin antagonist analogs, alpha-1 anti-trypsin (recombiniant).

Generally speaking, it is most preferable to use a water soluble form of the drug or agent to be delivered. Drug or agent precursors, i.e., species which generate the selected species by physical or chemical processes such as ionization, dissociation, or dissolution, are within the definition of "agent" or "drug" herein. "Drug" or "agent" is to be understood to include charged and uncharged species as described above.

EXAMPLE 1

An iontophoretic drug delivery device having the same configuration as the device illustrated in FIG. 6 is comprised of the following materials. ECA layers 64 each comprise 73 volume percent of a mixed polyisobutylene matrix (4 parts by volume of a low molecular weight PIB, and 1 part by volume of a high molecular weight PIB, as defined above) and 2 volume percent of a non-woven, carbon fiber mat. ECA layers 64 each also contain 25 volume percent of a water-conveying polymeric additive, namely, Polyplasdone XL, a cross-linked polyvinylpyrrolidone having a molecular weight in excess of 1,000,000. Thus ECA layers 64, in addition to being electrically conductive, are also water-conveying and thereby permit water applied to the top surfaces of ECA layers 64 to permeate therethrough to any underlying hydrophilic layers (e.g., reservoirs 24 and 25 and adhesive layers 27 and 28) and thereby, act as water wicking layers. ECA layers 64 are each adhered to an output of the circuit 32. Thus, one ECA layer 64 electrically connects circuit 32 to electrode 22 and the other ECA layer 64 electrically connects circuit 32 to electrode 23. In this example, electrode 22 is an anode, which is connected to the positive terminals of batteries 30. Electrode 23 is a cathode which is connected to the negative terminals of batteries 30.

Each of anode 22 and cathode 23 comprise a matrix of 55 volume percent of a 1:1 mixture of low and high molecular weight polyisobutylene and about 20 volume percent of cross-linked polyvinylpyrrolidone. In addition, anode 22 further includes about 25 volume percent silver powder while cathode 23 contains about 25 volume percent AgCl powder. An ion-impermeable and electrically insulating layer 26 comprised of ethylenevinylacetate, is interposed between electrode assemblies 18 and 19. Beneath and in intimate contact with anode 22 is drug reservoir 24. Drug reservoir 24 comprises 40 wt % of a 1:1 mixture of high and low molecular weight polyisobutylene, 35 wt % of metoclopramide Hcl, a water soluble drug salt, and 25 wt % cross-linked polyvinylpyrrolidone.

In intimate, contact with and beneath cathode 23 is salt reservoir 25. Salt reservoir 25 comprises 40 wt % of a 1:1 mixture of low and high molecular weight polyisobutylene (PIB), 30 wt % of NaCl, 25 wt % cross-linked polyvinylpyrrolidone and 5 wt % of a buffering agent. Skin contacting adhesive layers 27 and 28 are each comprised of about 70 volume percent of a 4:1 mixture of low and high molecular weight PIB and 30 volume percent of cross-linked polyvinylpyrrolidone.

EXAMPLE 2

A hydratible pressure sensitive ECA was made as follows. A polyisobutylene matrix was made by dry blending 40 parts by weight of previously mixed polyisobutylene matrix [comprised of 50 wt % low molecular weight PIB [about 35 kilo Daltons (kD)] and 50 wt % high molecular weight PIB [about 1.2 mega Daltons (MD)] with an additional 60 parts by weight of a low molecular weight PIB (about 35 kD) in a Brabender mixer having a 25 cm$^3$ mixing bowl at 20 rpm and heated to about 110° C. for about 30 minutes to form a uniform mixture. To this, 30 volume % powdered cross-linked hydrophilic polyvinylpyrrolidone resin (Polyplasdone XL sold by GAF Chemicals of Wayne, N.J.) was added to the mixing bowl over 5 minutes and was mixed for an additional 20 minutes. This mixture was then calendered using calender rolls heated to 90° C. to a thickness of 0.08 mm. One layer of this adhesive film was then laminated to a 5 g/m$^2$ non-woven carbon fiber mat, (sold by Veratec of Tuxedo, N.Y.) by passing the mat and the adhesive film between a set of opposed rolls heated to 90° C. Pressure was applied during this lamination such that the polymers flowed into the structure of the mat, and the resultant ECA film was tacky on both sides.

Six cathodic electrode assemblies having a structure similar to electrode assembly 19 shown in FIG. 6 were prepared using the ECA film described above. The ECA film layer 64 was laminated to a cathodic electrode layer 23 composed of 55 vol % of a hydrophobic polymer; 25 vol % of electro-chemically reducible silver chloride powder; and 20 vol % of a hydrophilic polyvinyl pyrrolidone resin (Polyplasdone XL). Three of the six electrode assemblies utilized a cathodic electrode having a thickness of 0.09 mm and the remainder utilized a cathodic electrode of the same composition but having a thickness of 0.16 mm. The cathodic electrode layer 23 was laminated to an electrolyte reservoir 25 having a thickness of 0.1 mm and composed of 40 wt % of a hydrophobic polymer resin; 30 wt % of an electrolyte salt (NaCl); 25 wt % hydrophilic polymer resin (Polyplasdone XL); and 3.5 wt % buffer. A skin contact adhesive layer 28 having a thickness of 0.08 mm was laminated to the electrolyte reservoir 25. The skin contact adhesive was composed of 80 vol % of a hydrophobic contact adhesive and 20 vol % hydrophilic polymer resin (Polyplasdone XL). In order to measure electric current levels passing through the electrode assemblies, an anodic electrode having a thickness of 0.15 mm and a composition comprising 55 vol % of a hydrophobic polymer; 25 vol % of electro-chemically oxidizable silver powder; and 20 vol % carbon fibers; was attached to the skin contact adhesive layer 28.

As a comparison, two cathodic electrode assemblies having the multi-laminate structure and compositions described above but having no ECA film layer 64 were also prepared.

The time required to hydrate the six electrode assemblies (electrode assemblies A through F in Table 1) utilizing the ECA film layer 64 and the two electrode assemblies (electrode assemblies G and H in Table 1) utilizing no ECA film layer was determined by placing a rubber gasket having an internal volume of 300 μl in fluid tight contact with the top-most layer (i.e., on the ECA layer 64 or on the electrode layer 23 for the two comparison assemblies) of the multi-laminate. A DC power source having a potential of about 8.5 volts was connected to the ECA layer 64 (in the assemblies A–F using an ECA layer) or to a silver foil (in the assemblies G and H using no ECA layer) and the anodic electrode using alligator clips. A computer controlled circuit board (DT 2801 series board controlled by Labtech Notebook 4.3 software; both sold by Data Translation of Marlborough, Mass.) was connected with the DC power source to measure the voltage drop across the electrode assembly and thereby calculate the amount of current passing through the electrode assembly. The rubber gasket was filled with water and the current passing through the electrode assembly was measured every minute over a period of about 4 hours. The times required to reach (i) 90% and (ii) 99% of the steady state current levels ($I_{ss}$) are presented in Table 1.

TABLE 1

| Electrode Assembly | Cathode Thickness (mm) | Time To 90% of $I_{SS}$ (minutes) | Time to 99% of $I_{SS}$ (minutes) |
|---|---|---|---|
| A | 0.16 | 63 | 65 |
| B | 0.16 | 48 | 49 |
| C | 0.16 | 56 | 59 |
| D | 0.09 | 40 | 41 |
| E | 0.09 | 43 | 43 |
| F | 0.09 | 46 | 48 |
| G | 0.09 | 36 | 38 |
| H | 0.09 | 38 | 39 |

The ECA film layer increased the time required to substantially hydrate an electrode assembly, as measured by the time to reach 90%/99% of steady state current levels, by only about 15% for electrode assemblies having cathodes of equivalent thickness. Even using the thicker cathodic electrodes, the time required to reach 99% of steady state current levels was never significantly longer than 1 hour. Moreover, the ECA layer provided little resistance to the passage of water through its structure to other dry but hydratable components such as the electrolyte reservoir 25 and the in-line skin contact adhesive layer 28. The ECA film layer 64 also provided good electrical conduction between the power source and the underlying electrode structure.

EXAMPLE 3

A nonhydratable ECA was made as follows. About 21.6 g of a preblended polyisobutylene matrix [4 parts of a low molecular weight PIB (about 35 kD) and 1 part of a high molecular weight PIB (about 1.2 MD)] was slowly charged over a period of 2 minutes into a Brabender mixer equipped with a 25 cm$^3$ mixing bowl. The initial temperature was ambient and the rotor speed was set at 10 rpm. Immediately after the addition of the PIB preblend, about 2.25 g of carbon black (Ketjenblack EC 600 JD made by AKZO Chemicals, Chicago, Ill.) was slowly added to the mixing bowl over a period of 3 minutes. The temperature of the mix at the end of the carbon black addition was 45° C. After the completion of the carbon black addition, the rotor speed was increased to 40 rpm and the materials were mixed for 20 additional minutes. The temperature at the end of the mix was 65° C. This mix was then calendered using calender rolls heated to 85° C. to a film thickness of 0.08 mm. The film had an electrical resistivity of 200 ohm-cm when measured using a Loresta AP 4 point probe, Model No. MCP-T400 (sold by Optical Associates, Inc, Milpitas, Calif.).

EXAMPLE 4

A hydratable pressure sensitive ECA was made as follows. First, 17.06 g of the same 4:1 low to high molecular weight PIB matrix preblend used in Example 3 was charged into the Brabender mixer under ambient conditions and 20 rpm rotor speed. After one minute, a powder preblend of 20 vol % Polyplasdone XL and 5 vol % Ketjenblack EC 600 JD was slowly added to the mixing bowl. The total time to add 5.73 g of Polyplasdone XL and 2.25 g of carbon black was 16 minutes and the total mix time was 20 minutes. This mix was then calendered using calender rolls heated to 93° C. to a thickness of 0.13 mm. The resistivity of the film was 20 ohm-cm measured using the Loresta AP 4 point probe.

The above disclosure will suggest many alternatives, permutations, and variations of the invention to one of skill in this art. This disclosure is intended to be illustrative and not exhaustive. All such, permutations, variations and alternative suggested by the above disclosure are to be included within the scope of the attached claims.

What is claimed is:

1. An iontophoretic agent delivery device comprising a pair of electrode assemblies, a least one of said electrode assemblies having a donor electrode and a reservoir for containing the agent to be iontophoretically delivered, said reservoir being adapted to be placed in agent transmitting relation with a body surface through which said agent is to be delivered, an electronic circuit having a plurality of electronic components including a source of electrical energy, and having a circuit output which is electrically connected to said reservoir, said electronic circuit being capable of controlling the electric current applied by the device, said device having an electrically conductive pressure sensitive adhesive wherein the adhesive is conducting in all directions, the adhesive being in direct physical and electrical contact with said circuit output and the adhesive also being in electrical contact with at least one member selected from the group consisting of an electrode assembly, an electrode and a reservoir, said adhesive comprising at least a portion of the electrical connection between the circuit output and the reservoir.

2. The device of claim 1 wherein the adhesive contains an electrochemically reactive species.

3. The device of claim 2, wherein the adhesive comprises (i) an anodic electrode and the electrochemically reactive species is capable of undergoing electrochemical oxidation; and/or (ii) a cathodic electrode and the electrochemically reactive species is capable of undergoing electrochemical reduction.

4. The device of claim 1, wherein the adhesive is flexible.

5. The device of claim 4, wherein the adhesive is in the form of a flexible film or sheet.

6. The device of claim 1, wherein the adhesive comprises an adhesive matrix containing a conductive filler.

7. The device of claim 6 wherein the adhesive matrix comprises low molecular weight polyisobutylene and high molecular weight polyisobutylene in a volume ratio of about 6:1 to about 2:1.

8. The device of claim 6, wherein the conductive filler is selected from the group consisting of: a conductive particulate material, a conductive fibrous material, a conductive web, a conductive mat, a conductive mesh, carbon particles, carbon fibers, metal particles, and metal flakes.

9. The device of claim 1, wherein the adhesive has a resistivity of less than about $1.3 \times 10^5$ ohm-cm.

10. The device of claim 1 wherein the adhesive contains an agent to be iontophoretically delivered.

11. The device of claim 1, wherein at least one of said electrode assemblies is an anode and at least one of said electrode assemblies is a cathode.

12. The device of claim 11 wherein said adhesive is in the form of a film, sheet, or web and said film, sheet or web has an opening therein.

13. The device of claim 12, wherein said adhesive contacts said electrodes along a peripheral edge of a surface thereof.

14. The device of claim 1, wherein the adhesive contains a liquid solvent retaining additive.

15. The device of claim 14, wherein the additive is a hydrophilic polymer.

16. The device of claim 14 or 15, including a liquid releasing means in fluid communication with said adhesive.

17. The device of claim 15, wherein the hydrophilic polymer is cross-linked.

18. An iontophoretic agent delivery device comprising a reservoir, for containing the agent to be iontophoretically delivered, said reservoir being adapted to be placed in agent transmitting relation with a body surface through which said agent is to be delivered, an electronic circuit having a plurality of electronic components including a source of electrical energy, and having a circuit output which is electrically connected to said reservoir said electronic circuit being capable of controlling the level of electric current applied by the device, said device being characterized by an electrically conductive adhesive in direct electrical contact with said circuit output said adhesive comprising at least a portion of the electrical connection of the circuit output to the reservoir, including an anode and a cathode, and said outputs being connected to said anode and said cathode by said adhesive, said adhesive comprising a flexible, electrically conductive adhesive which adheres to said circuit outputs and said electrodes, in at least a portion thereof, to connect said circuit outputs and said electrodes, wherein said adhesive is in the form of a film, sheet or web, said film, sheet or web having an opening therein, and wherein a wicking material is positioned in the opening.

19. The device of claim 18, including a liquid releasing means in fluid communication with said wicking material.

20. An iontophoretic agent delivery device comprising a pair of electrode assemblies, a least one of said electrode assemblies having a donor electrode and a reservoir for containing the agent to be iontophoretically delivered, said reservoir being adapted to be placed in agent transmitting relation with a body surface through which said agent is to be delivered, an electronic circuit having a plurality of electronic components including a source of electrical energy, and having a circuit output which is electrically connected to said reservoir, said electronic circuit being capable of controlling the electric current applied by the device, said device having an electrically conductive pressure sensitive adhesive wherein said adhesive is electrically conducting in all directions, in direct physical and electrical contact with said circuit output and the adhesive also being in electrical contact with at least one member selected from the group consisting of an electrode assembly, an electrode and a reservoir, said adhesive comprising at least a portion of the electrical connection between the circuit output and the reservoir wherein said adhesive has a resistivity of less than about $1.5 \times 10^5$ ohm-cm.

21. An iontophoretic agent delivery device comprising a pair of electrode assemblies, a least one of said electrode assemblies having a donor electrode and a reservoir for containing the agent to be iontophoretically delivered, said reservoir being adapted to be placed in agent transmitting relation with a body surface through which said agent is to be delivered, an electronic circuit having a plurality of electronic components including a source of electrical energy, and having a circuit output which is electrically connected to said reservoir, said electronic circuit being capable of controlling the electric current applied by the device, said device having an electrically conductive pressure sensitive adhesive wherein said adhesive is electrically conductive in all directions, in direct physical and electrical contact with said circuit output and the adhesive also being in electrical contact with at least one member selected from the group consisting of an electrode assembly, an electrode and a reservoir, said adhesive comprising at least a portion of the electrical connection between the circuit output and the reservoir wherein said adhesive comprises a carbon conductive filler.

22. The device of claim 21, wherein the conductive filler has an iodine absorption number greater than 750 mg/g.

23. The device of claim 21, wherein the conductive filler has an iodine absorption number greater than 1000 mg/g.

24. The device of claim 21, wherein the conductive filler comprises 5 percent by volume or less.

* * * * *